United States Patent
Jeon et al.

(10) Patent No.: US 7,425,656 B2
(45) Date of Patent: Sep. 16, 2008

(54) PHOSPHORUS-CONTAINING CATALYST COMPOSITION AND PROCESS FOR HYDROFORMYLATION REACTION USING THE SAME

(75) Inventors: You Moon Jeon, Daejeon (KR); Donghyun Ko, Daejeon (KR); Sungshik Eom, Daejeon (KR); O Hak Kwon, Daejeon (KR); Jaehui Choi, Anyang (KR)

(73) Assignee: LG Chem, Ltd (KR)

( * ) Notice: Subject to any disclaimer, the term of this patent is extended or adjusted under 35 U.S.C. 154(b) by 0 days.

(21) Appl. No.: 11/227,479

(22) Filed: Sep. 15, 2005

(65) Prior Publication Data

US 2006/0058558 A1 Mar. 16, 2006

(30) Foreign Application Priority Data

Sep. 15, 2004 (KR) .................. 10-2004-0073919

(51) Int. Cl.
*C07C 45/00* (2006.01)
(52) U.S. Cl. .................. 568/454; 548/402; 556/13; 564/12; 502/162
(58) Field of Classification Search .............. 568/454; 548/402; 556/13; 564/12; 502/162
See application file for complete search history.

(56) References Cited

U.S. PATENT DOCUMENTS

| | | | | |
|---|---|---|---|---|
| 4,668,651 | A | 5/1987 | Billig et al. .............. | 502/158 |
| 4,687,874 | A | 8/1987 | Oswald et al. .............. | 568/454 |
| 4,694,109 | A | 9/1987 | Devon et al. .............. | 568/454 |
| 5,763,679 | A * | 6/1998 | Nicholson et al. .......... | 568/454 |
| 5,777,087 | A * | 7/1998 | Kohlpaintner et al. ....... | 534/14 |
| 5,874,640 | A * | 2/1999 | Bryant et al. .............. | 568/454 |
| 5,917,095 | A * | 6/1999 | Bryant et al. .............. | 568/454 |
| 5,962,744 | A | 10/1999 | Ojima et al. .............. | 568/454 |
| 6,043,398 | A * | 3/2000 | Kohlpaintner et al. ....... | 568/454 |
| 6,653,485 | B2 * | 11/2003 | Zhang .................. | 549/221 |
| 7,084,293 | B2 * | 8/2006 | Rosier et al. .............. | 558/335 |

FOREIGN PATENT DOCUMENTS

| | | |
|---|---|---|
| EP | 0 580 358 A1 | 1/1994 |
| EP | 0 918 781 B1 | 12/1997 |
| WO | WO0240491 | * 5/2002 |

OTHER PUBLICATIONS

Chen et al., {Application of phosphinous amide ligands in palladium complex-catalyzed asymmetric allylic alkylation: influence of steric effects on enantioselectivity, Tetrahedron: Asymmetry (2004), 15(2), 213-217}.*
Chen et al., {Novel chiral aminophosphine ligand: synthesis and application in asymmetric catalytic hydrogenation reaction, Chinese Journal of Chemistry (2003), 21(1), 66-70}.*
Guo et al., {Rhodium-catalyzed asymmetric hydrogenation with aminophosphine ligands derived from 1,1'-binaphthyl-2,2'-diamine, Tetrahedron Letters (2002), 43(38), 6803-6806}.*
Zhang et al., {Asymmetric Synthesis of Chiral Amine Derivatives through Enantioselective Hydrogenation with a Highly Effective Rhodium Catalyst Containing a Chiral Bisaminophosphine Ligand, Journal of the American Chemical Society (1998), 120(23), 5808-5809}.*
Miyano et al., {Axially dissymmetric bis(aminophosphine)s derived from 2,2'-diamino-1,1'-binaphthyl. Synthesis and application to rhodium(I)-catalyzed asymmetric hydrogenations, Bulletin of the Chemical Society of Japan, (1984), 57(8), 2171-6}.*
Miyano et al., Axially dissymmetric bis(aminophosphine)s derived from 2,2'-diamino-1,1'-binaphthyl. Synthesis and application to rhodium(I)-catalyzed asymmetric hydrogenations, Bulletin of the Chemical Society of Japan, (1984), 57(8), 2171-2176.*
CEH Marketing Research Report, OXO CHEMICALS; Authors: Sebastian N. Bizzari, Ralf Gubler, and Akihiro Kishi; Chemical Economics Handbook- SRI International, Nov. 2002 (121 pages).

* cited by examiner

*Primary Examiner*—Yvonne (Bonnie) Eyler
*Assistant Examiner*—Chukwuma O. Nwaonicha
(74) *Attorney, Agent, or Firm*—Cantor Colburn LLP

(57) ABSTRACT

Provided are a catalyst composition including a transition metal catalyst and a nitrogen-containing bidentate phosphorus compound and a process for hydroformylation reaction of olefins to prepare aldehydes which includes stirring the catalyst composition, an olefin compound, and a gas mixture of of carbon monoxide and hydrogen, under high temperature and pressure condition. Therefore, very high catalytic activity and high selectivity in normal-aldehyde or iso-aldehyde according to the type of a substiuent are ensured.

11 Claims, No Drawings

PHOSPHORUS-CONTAINING CATALYST COMPOSITION AND PROCESS FOR HYDROFORMYLATION REACTION USING THE SAME

CROSS-REFERENCE TO RELATED PATENT APPLICATION

This application claims priority from Korean Patent Application No. 10-2004-0073919, filed on Sep. 15, 2004, in the Korean Intellectual Property Office, the disclosure of which is incorporated herein in its entirety by reference.

FIELD OF THE INVENTION

The present invention relates to a hydroformylation reaction catalyst composition including a bidentate phosphorus compound and a process for hydroformylation reaction using the same. More particularly, the present invention relates to a process for hydroformylation reaction of olefins to prepare aldehydes which includes stirring a transition metal catalyst modified with a nitrogen-containing bidentate phosphorus compound ligand, an olefin compound, and a mixed gas of carbon monoxide and hydrogen, under high temperature and pressure condition.

DESCRIPTION OF THE RELATED ART

Generally, hydroformylation reaction, also well known as an oxo reaction, is a process in which an olefin reacts with a synthesis gas ($CO/H_2$) in the presence of a metal catalyst and a ligand to produce a linear (normal) or branched (iso) aldehyde which has one more carbon atom than the olefin. The oxo reaction was originally discovered in 1938 by a German scientist, Otto Roelen. About 8,400,000 tons of aldehydes (including alcohol derivatives) were produced by oxo reaction and consumed around the world in 2001 (*SRI report*, November 2002, 682. 7000A). Aldehydes produced by the oxo reaction are oxidized or reduced to their corresponding derivatives, acids or alcohols. In addition, aldehydes can also be converted to long alkyl chain-containing acids or alcohols through aldol condensation and then oxidation or reduction. The alcohols and acids thus produced are used as solvents, additives, materials of various plasticizers, etc.

Currently, cobalt and rhodium catalysts are mainly used in an oxo process. The N/I (ratio of linear (normal) to branched (iso) isomers) selectivity of aldehydes varies according to the type of ligand used and operating conditions. To date, a rhodium-catalyzed, low-pressure oxo process has been adopted in at least 70% of oxo plants worldwide.

In addition to cobalt (Co) and rhodium (Rh), iridium (Ir), ruthenium (Ru), osmium (Os), platinum (Pt), palladium (Pd), iron (Fe), nickel (Ni), etc. can be used as a central metal of an oxo catalyst. However, since it is known that the descending order of catalytic activity is as follows: Rh>>Co>Ir, Ru>Os>Pt>Pd>Fe>Ni, most processes and studies have been focused on rhodium and cobalt. A ligand of the oxo catalyst may be phosphine ($PR_3$, $R=C_6H_5$, $n\text{-}C_4H_9$), phosphine oxide ($O=P(C_6H_5)_3$), phosphite, amine, amide, isonitrile, etc. However, there are few ligands superior to triphenylphosphine (TPP) considering catalytic activity, stability, and costs. Thus, a rhodium catalyst modified with a TPP ligand is used in most oxo processes. Furthermore, it is known that a TPP ligand is used in an amount of 100 eq. or more based on rhodium metal present in the rhodium complex catalyst to increase catalyst stability.

The Eastman Kodak Company and the Union Carbide Company (now a subsidiary of the Dow Chemical Company) developed a bidentate phosphine ligand imparting high activity and N/I selectivity to a catalyst, respectively. (U.S. Pat. Nos. 4,694,109 and 4,668,651). It is known that a bisphosphite ligand developed by the Dow Chemical Company has been used in some plants.

U.S. Pat. No. 6,653,485 discloses an asymmetric reaction using a chiral biaryl phosphine or phosphinite ligand and a transition metal catalyst. Even though this patent discloses that a nitrogen-containing bidentate phosphorous compound can be used as the ligand, it is silent about the actual application of the nitrogen-containing bidentate phosphorous compound in hydroformylation reaction.

The industrial importance of normal aldehydes is currently remarkably increasing. Thus, a catalyst composition that exhibits a high selectivity to normal-aldehyde or iso-aldehyde, and high catalytic activity at high temperature is needed.

SUMMARY OF THE INVENTION

The present invention provides a catalyst composition including a bidentate ligand and a transition metal catalyst which exhibits high catalytic activity and N/I selectivity.

The present invention also provides a process for hydroformylation reaction of an olefin compound to prepare an aldehyde which includes stirring the catalyst composition, the olefin compound, and a gas mixture of of carbon monoxide and hydrogen, under high temperature and pressure condition.

The present invention also provides a compound used as the bidentate ligand.

The present invention also provides a process for preparing the compound used as the bidentate ligand.

According to an aspect of the present invention, there is provided a catalyst composition including:

(a) a bidentate ligand represented by formula 1 below; and (b) a transition metal catalyst represented by formula 2 below:

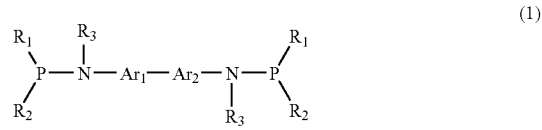

(1)

wherein, $R_1$ and $R_2$ are each a substituted or unsubstituted alkyl group of 1-20 carbon atoms, a substituted or unsubstituted alkoxy group of 1-20 carbon atoms, a substituted or unsubstituted cycloalkane or cycloalkene of 5-20 carbon atoms, a substituted or unsubstituted aryl group of 6-36 carbon atoms, a substituted or unsubstituted heteroalkyl group of 1-20 carbon atoms, a substituted or unsubstituted heteroaryl group of 4-36 carbon atoms, or a substituted or unsubstituted hetero ring group of 4-36 carbon atoms;

$Ar_1\text{-}Ar_2$ is a bisaryl compound; and $R_3$ is an alkyl group of 1-20 carbon atoms, an aryl group of 6-20 carbon atoms, a triarylsilyl group, a trialkylsilyl group, a carboalkoxy group represented by $-CO_2R$ where R is an alkyl group of 1-20 carbon atoms or an aryl group of 6-20 carbon atoms, a carboaryloxy group, an aryloxy group, an alkoxy group, an alkylcarbonyl group, an arylcarbonyl group, an amide, a halogen, or a nitrile group, and $$M(L_1)_l(L_2)_m(L_3)_n \quad (2)$$

wherein,

M is a transition metal;

$L_1$, $L_2$ and $L_3$ are each hydrogen, CO, acetylacetonato, cyclooctadiene, norbornene, chlorine, or triphenylphosphine; and l, m, and n are each an integer of 0 to 5, and the sum of l, m and n is not zero.

According to another aspect of the present invention, there is provided a process for hydroformylation reaction of an olefin compound to prepare an aldehyde which includes stirring the catalyst composition, the olefin compound, and a gas mixture of of carbon monoxide and hydrogen, under high temperature and pressure condition.

The olefin compound may be a compound represented by formula 3 below:

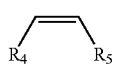

(3)

wherein, $R_4$ and $R_5$ are each hydrogen, an alkyl group of 1-20 carbon atoms, fluorine (—F), chlorine (—Cl), bromine (—Br), trifluoromethyl (—CF$_3$), or a phenyl group of 6-20 carbon atoms that may be unsubstituted or substituted by one to five substituents selected from the group consisting of a nitro group (—NO$_2$), fluorine (—F), chlorine (—Cl), bromine (—Br), a methyl group, an ethyl group, a propyl group, and a butyl group.

According to still another aspect of the present invention, there is provided a compound represented by formula 1 below:

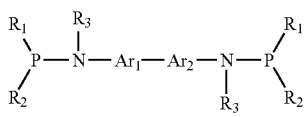

(1)

wherein, $R_1$, $R_2$, $R_3$, and Ar$_1$—Ar$_2$ are as defined above.

According to yet another aspect of the present invention, there is provided a process for preparing the compound of formula 1, the process including:

reacting a compound represented by formula 4 below with a base to obtain an amine salt; and reacting the amine salt with a compound represented by XPR$_1$R$_2$ where X is a halogen and R$_1$ and R$_2$ are as defined above to obtain a bidentate compound with a direct phosphorus-nitrogen bond:

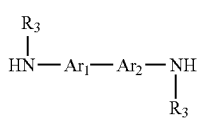

(4)

wherein,

R$_3$ and Ar$_1$—Ar$_2$ are as defined above.

DETAILED DESCRIPTION OF THE INVENTION

The present invention provides a catalyst composition including a bidentate ligand and a transition metal catalyst.

The bidentate ligand represented by formula 1 may be a bidentate ligand in which $R_1$ and $R_2$ are each a phenyl group, a phenyloxy group, an alkyl group, an alkyloxy group, or a pyrrole group, and $R_3$ is a methyl group, an ethyl group, a phenyl group, or an acetyl group.

The bisaryl compound of formula 1 may be a compound represented by formula 5 or 6 below:

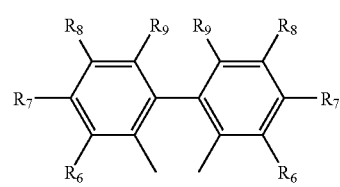

(5)

wherein, $R_6$, $R_7$, $R_8$, and $R_9$ are each hydrogen, an alkyl group of 1-20 carbon atoms, an aryl group of 6-20 carbon atoms, a triarylsilyl group, a trialkylsilyl group, a carboalkoxy group represented by —CO$_2$R where R is an alkyl group of 1-20 carbon atoms or an aryl group of 6-20 carbon atoms, a carboaryloxy group, an aryloxy group, an alkoxy group, an alkylcarbonyl group, an arylcarbonyl group, an amide, a halogen, or a nitrile group, and preferably, $R_6$ is a methyl group, a methoxy group, a tert-butyl group, $R_7$ is hydrogen, $R_8$ is a methyl group, a methoxy group, or a tert-butyl group, and $R_9$ is hydrogen or a methyl group,

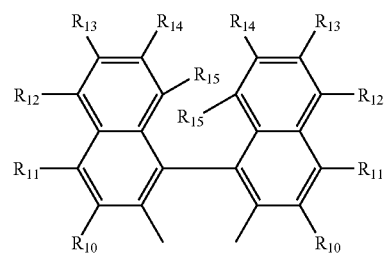

(6)

wherein, $R_{10}$, $R_{11}$, $R_{12}$, $R_{13}$, $R_{14}$, and $R_{15}$ are each hydrogen, an alkyl group of 1-20 carbon atoms, an aryl group of 6-20 carbon atoms, a triarylsilyl group, a trialkylsilyl group, a carboalkoxy group represented by —CO$_2$R where R is an alkyl group of 1-20 carbon atoms or an aryl group of 6-20 carbon atoms, a carboaryloxy group, an aryloxy group, an alkoxy group, an alkylcarbonyl group, an arylcarbonyl group, an amide, a halogen, or a nitrile group.

In the transition metal catalyst, the transition metal M may be cobalt (Co), rhodium (Rh), or iridium (Ir). More specifically, the transition metal catalyst may be acetylacetonatodicarbonylrhodium (Rh(AcAc)(CO)$_2$), acetylacetonatocarbonyltriphenylphosphinerhodium (Rh(AcAc)(CO)(TPP)), hydridocarbonyltri(triphenylphosphine)rhodium (HRh(CO)(TPP)$_3$), acetylacetonatodicarbonyliridium (Ir(AcAc)(CO)$_2$), or hydridocarbonyltri(triphenylphosphine)iridium (HIr(CO)(TPP)$_3$).

In the catalytic reaction of the present invention, the content of the transition metal may be in the range from 50 to 500 ppm based on a reactant solution. If the content of the transition metal is less than 50 ppm, hydroformylation reaction may be retarded, which restricts industrial application. On the other hand, if it exceeds 500 ppm, process costs increase due to the increased use of an expensive transition metal. Furthermore, a reaction rate is not increased in proportion to the increased amount of the transition metal.

The content of the bidentate ligand is in the range from 0.5 to 100 moles, preferably from 1 to 20 moles, based on 1 mole of the transition metal. If the content of the bidentate ligand is less than 0.5 moles, the stability of a catalyst system may be lowered. On the other hand, if it exceeds 100 moles, the increased use of the expensive ligand without additional benefits may increase process costs.

Particularly preferably, the transition metal catalyst is acetylacetonatodicarbonylrhodium (Rh(AcAc)(CO)$_2$), and the bidentate ligand is 2,2'-bis[N-(diphenylphosphino)methylamino]-1,1'-bipehnyl (BPNP-1).

The olefin compound may be a compound selected from the group consisting of ethene, propene, 1-butene, 1-pentene, 1-hexene, 1-octene, and styrene.

A solvent that can be used in the hydroformylation reaction of the present invention may be aldehydes such as propionaldehyde, butyraldehyde, and valeraldehyde; ketones such as acetone, methylethylketone, methylisobutylketone, acetophenone, and cyclohexanone; aromatics such as benzene, toluene, and xylene; halogenated aromatics such as orthodichlorobenzene; ethers such as tetrahydrofuran, dimethoxyethane, and dioxane; halogenated paraffins such as methylene chloride; paraffin hydrocarbons such as heptane; etc. Aldehydes and aromatics such as toluene are preferable.

The composition of the syngas (CO/H$_2$) used in the hydroformylation reaction of the present invention may be changed within a broad range. Generally, the molar ratio of CO/H$_2$ is in the range from about 5:95 to 70:30, preferably from about 40:60 to 60:40, particularly preferably about 1:1.

Generally, the hydroformylation reaction is performed at a temperature of about 20 to 180° C., preferably about 50 to 150° C., and at a pressure of about 1 to 700 bar, preferably 1 to 300 bar.

A process for preparing the compound of formula 1 will now be described in detail. First, a compound of formula 4 below is dissolved in a solvent, and a base such as n-butyl lithium is added to the reactant solution with cooling to 0° C. or less to obtain an amine salt. A compound represented by XPR$_1$R$_2$ (where X is a halogen, and R$_1$ and R$_2$ are as defined above) is dropwise added to the amine salt solution, and the resultant precipitate is then filtered, purified, and dried, to obtain a bidentate compound with a direct phosphorus-nitrogen bond as represented by formula 1.

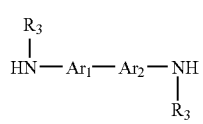

(4)

wherein,

R$_3$ and Ar$_1$—Ar$_2$ are as defined above.

In the preparation of the compound of formula 1, the solvent may be tetrahydrofuran (THF), benzene, toluene, ether, dichloromethane, etc. THF is particularly preferable. The base may be selected from the group consisting of n-butyl lithium, tert-butyl lithium, sodium hydride (NaH), potassium hydride (KH), triethylamine, and pyridine.

In the compound represented by XPR$_1$R$_2$, X may be chlorine (Cl), bromine (Br), or iodine (I), R$_1$ and R$_2$ may each be a phenyl group, a phenyloxy group, an alkyl group, or an alkyloxy group.

A catalyst composition according to the present invention including a nitrogen-containing bidentate phosphorus compound ligand exhibits very high catalytic activity, and at the same time high selectivity to normal-aldehyde or iso-aldehyde according to the type of a substituent in the hydroformylation reaction of an olefin compound.

Hereinafter, the present invention will be described more specifically with reference to the following examples. The following examples are for illustrative purposes and are not intended to limit the scope of the invention.

SYNTHESIS EXAMPLE 1

Synthesis of 2,2'-bis[N-(diphenylphosphino)methylamino]-1,1'-biphenyl (BPNP-1)

1.5 g of 2,2'-bismethylamino-1,1'-bipheny was dissolved in an anhydrous tetrahydrofuran solvent. 6.5 mL of a n-butyl lithium (2.5 M) solution was added to the reactant solution with cooling with ice water and stirred for 30 minutes. Then, 15 mL of an anhydrous tetrahydrofuran solution containing 3.1 mL of chlorodiphenylphosphine was dropwise added to the reactant solution with stirring and the resulting solution was stirred at room temperature overnight. A precipitate was filtered, and a solvent was removed from the remaining solution under a reduced pressure. The resultant precipitate was washed with a small quantity of purified ethanol and dried in a vacuum to give 2.66 g (yield 65%) of the titled compound. The titled compound was dissolved in chloroform-D (CDCl$_3$) to perform the hydrogen and phosphorus nuclear magnetic resonance (NMR) spectrum analysis for the titled compound. The NMR analysis results were as follows: $^1$H NMR (CDCl$_3$): δ 2.52 (s, 6H, —CH$_3$), 6.81-7.32 (m, 28H, Ar—H). $^{31}$P NMR (CDCl$_3$): δ 54.39 (s).

SYNTHESIS EXAMPLE 2

Synthesis of 2,2'-bis[N-(dipyrrolylphosphino)methylamino]-1,1'-biphenyl (BPNP-2)

The titled compound was synthesized in the same manner as in Synthesis Example 1 except that chlorodipyrrolylphosphine was used instead of chlorodiphenylphosphine. The titled compound was dissolved in chloroform-D (CDCl$_3$) to perform the hydrogen NMR spectrum analysis for the titled compound. The NMR analysis result was as follows: $^1$H NMR (CDCl$_3$): δ 2.58 (bs, 3H, —CH$_3$), 3.04 (bs, 3H, —CH$_3$), 6.24 (t, 2H, -py), 6.45 (t, 6H, -py), 6.82 (m, 2H, -py), 6.89 (m, 6H, -py), 7.32-7.40 (m, 8H, Ar—H).

EXAMPLES 1-4

Hydroformylation reaction of propene using acetylacetonatodicarbonylrhodium (Rh(AcAc)(CO)$_2$) and 2,2'-bis[N-(diphenylphosphino)methylamino]-1,1'-biphenyl (BPNP-1)

0.100 mg (0.390 mmol) of a Rh(AcAc)(CO)$_2$ catalyst, 0.2 mL of hexadecane which was an internal standard for GC analysis, and BPNP-1 as bidentate ligand, according to its molar ratio relative to rhodium presented in Table 1 below were dissolved in a toluene solvent until the total volume of the reactant solution reached 100 mL, and charged into a high throughput screen (HTS) unit manufactured by the Autoclave company. A reaction gas of propene, CO, and $H_2$ (1:1:1, molar ratio) was injected to the reactant solutiont to maintain a pressure at 6 bar, and then the reactant solution was stirred at a temperature of 85° C. for 2.5 hours.

The types of the catalyst and the ligand used, the molar ratio of the ligand to the catalyst, the N/I selectivity, and the catalytic activity are listed in Table 1 below.

In Table 1, the N/I selectivity value is the production ratio of normal-butyraldehyde to iso-butyraldehyde. The production amount of each aldehyde was calculated based on the amount of hexadecane used as the internal standard for the GC analysis.

The catalytic activity was obtained by dividing the total amount of normal-butyraldehyde and iso-butyraldehyde produced by the molecular weight of butyraldehyde, the concentration of the used catalyst, and the reaction time. The unit of the catalytic activity was $mol_{(BAL)}/mol_{(Rh)}/h$.

TABLE 1

| Example | Catalyst | Ligand (L) | L/Rh (mol/mol) | N/I | Catalytic activity ($mol_{(BAL)}/mol_{(Rh)}/h$) |
|---|---|---|---|---|---|
| Example 1 | $Rh(AcAc)(CO)_2$ | BPNP-1 | 1 | 1.8 | 169.5 |
| Example 2 | $Rh(AcAc)(CO)_2$ | BPNP-1 | 3 | 23.2 | 145.6 |
| Example 3 | $Rh(AcAc)(CO)_2$ | BPNP-1 | 5 | 23.6 | 139.9 |
| Example 4 | $Rh(AcAc)(CO)_2$ | BPNP-1 | 10 | 23.0 | 136.0 |

EXAMPLES 5-9

Hydroformylation reaction of propene with respect to reaction temperature using acetylacetonatodicarbonylrhodium ($Rh(AcAc)(CO)_2$) and 2,2'-bis[N-(diphenylphosphino)methylamino]-1,1'-biphenyl (BPNP-1)

Catalytic activity experiments were performed in the same manner as in Example 1 except that the molar ratio of the ligand to rhodium was fixed to 3 and the reaction temperature was changed from 70 to 110° C. while increasing the temperature by 10° C. increments. The results are presented in Table 2 below.

TABLE 2

| Example | Catalyst | Ligand (L) | L/Rh (mol/mol) | Temp. (° C.) | N/I | Catalytic activity ($mol_{(BAL)}/mol_{(Rh)}/h$) |
|---|---|---|---|---|---|---|
| Example 5 | $Rh(AcAc)(CO)_2$ | BPNP-1 | 3 | 70 | 23.1 | 50.4 |
| Example 6 | $Rh(AcAc)(CO)_2$ | BPNP-1 | 3 | 80 | 24.8 | 102.7 |
| Example 7 | $Rh(AcAc)(CO)_2$ | BPNP-1 | 3 | 90 | 27.1 | 168.4 |
| Example 8 | $Rh(AcAc)(CO)_2$ | BPNP-1 | 3 | 100 | 31.1 | 253.8 |
| Example 9 | $Rh(AcAc)(CO)_2$ | BPNP-1 | 3 | 110 | 27.8 | 275.1 |

EXAMPLES 10-13

Hydroformylation reaction of propene using acetylacetonatodicarbonylrhodium ($Rh(AcAc)(CO)_2$) and 2,2'-bis[N-(dipyrrolylphosphino)methylamino]-1,1'-biphenyl (BPNP-2)

Catalytic activity experiments were performed in the same manner as in Examples 1-4 except that BPNP-2 was used instead of BPNP-1, and the results are presented in Table 3 below.

TABLE 3

| Example | Catalyst | Ligand (L) | L/Rh (mol/mol) | N/I | Catalytic activity ($mol_{(BAL)}/mol_{(Rh)}/h$) |
|---|---|---|---|---|---|
| Example 10 | $Rh(AcAc)(CO)_2$ | BPNP-2 | 1 | 1.2 | 188.2 |
| Example 11 | $Rh(AcAc)(CO)_2$ | BPNP-2 | 3 | 1.5 | 198.2 |
| Example 12 | $Rh(AcAc)(CO)_2$ | BPNP-2 | 5 | 2.2 | 144.6 |
| Example 13 | $Rh(AcAc)(CO)_2$ | BPNP-2 | 10 | 3.6 | 62.5 |

COMPARATIVE EXAMPLE 1

Hydroformylation reaction of propene using acetylacetonatodicarbonylrhodium ($Rh(AcAc)(CO)_2$) and triphenylphosphine (TPP)

A catalytic activity experiment was performed in the same manner as in Example 1 except that TPP was used as a ligand and the molar ratio of the ligand to rhodium was 100, and the results are presented in Table 4 below.

COMPARATIVE EXAMPLES 2-3

Hydroformylation reaction of propene with respect to temperature using acetylacetonatodicarbonylrhodium ($Rh(AcAc)(CO)_2$ and triphenylphosphine (TPP)

Catalytic activity experiments were performed in the same manner as in Comparative Example 1 except that the reaction temperature was 70° C. (Comparative Example 2) and 100° C. (Comparative Example 3), and the results are presented in Table 4 below.

COMPARATIVE EXAMPLE 4

Hydroformylation reaction of propene using acetylacetonatodicarbonylrhodium ($Rh(AcAc)(CO)_2$) and ISO-44

A catalytic activity experiment was performed in the same manner as in Comparative Example 1 except that a bisphosphite ligand, 6,6'-[[3,3'-bis(1,1-dimethylehtyl)-5,5'-dimethoxy-[1,1'-biphenyl]-2,2'-diyl]bis(oxy)]bis-di benzo[d,f][1,3,2]dioxaphosphine (ISO-44, Dow) was used instead of TPP, and the molar ratio of the ligand to rhodium was 5, and the results are presented in Table 4.

COMPARATIVE EXAMPLES 5-6

Hydroformylation reaction of propene using acetylacetonatodicarbonylrhodium (Rh(AcAc)(CO)$_2$) and BISBI Catalytic activity experiments were performed in the same manner as in Comparative Example 1 except that 2,2'-bis(diphenylphosphinomethyl)-1,1'-biphenyl (BISBI) was used instead of TPP, and the molar ratio of the ligand to rhodium was 3 (Comparative Example 5) and 10 (Comparative Example 6), and the results are presented in Table 4 below.

COMPARATIVE EXAMPLE 7

Hydroformylation reaction of propene using acetylacetonatodicarbonylrhodium (Rh(AcAc)(CO)$_2$) and 2,2'-bis[N-(diphenylphosphino)amino]-1,1'-biphenyl (BPNP-0)

A catalytic activity experiment was performed in the same manner as in Comparative Example 1 except that BPNP-0 was used instead of TPP, and the molar ratio of the ligand to rhodium was 1, and the results are presented in Table 4 below.

N/I selectivity of 20 or more was observed, but catalytic activity was relatively low. In particular, as the molar ratio of the ligand to rhodium increased, the catalytic activity was gradually reduced.

In addition, in Comparative Example 7 using as a ligand 2,2'-bis[N-(diphenylphosphino)amino]-1,1'-biphenyl (BPNP-0), i.e., a compound in which a methyl group attached to a nitrogen of BPNP-1 was substituted by hydrogen, catalytic activity was very low. Furthermore, in experiments performed in the same manner as in Comparative Example 7 except that the molar ratio of the ligand to rhodium was 3 or more, no aldehydes were observed due to very low catalytic activity.

In Examples 2-4, in which 2,2'-bis[N-(diphenylphosphino)methylamino]-1,1'-biphenyl (BPNP-1) according to the present invention was used as a ligand, and the molar ratio of BPNP-1 to rhodium was 3 or more, the average catalytic activity was 165% higher than when Rh/TPP was used. N/I selectivity was about 23, which was 5.9 times higher selectivity to normal-aldehyde than when Rh/TPP was used. From these results, it can be seen that even the use of a small quantity of BPNP-1 ensures very high catalytic activity and high N/I selectivity. Even when the molar ratio of the ligand to rhodium was increased from 3 to 10, no reduction in catalytic activity was observed. This is in contrast to the Eastman Kodak report in which catalytic activity rapidly reduced as the amount of BISBI increased under the same conditions (U.S. Pat. No. 4,694,109).

In comparison between Comparative Example 4 using ISO-44 and Example 3 using BPNP-1 under the same condi-

TABLE 4

| Section | Catalyst | Ligand (L) | L/Rh (mol/mol) | Temp. (° C.) | N/I | Catalytic activity (mol$_{(BAL)}$/mol$_{(Rh)}$/h) |
|---|---|---|---|---|---|---|
| Comparative Example 1 | Rh(AcAc)(CO)$_2$ | TPP | 100 | 85 | 3.9 | 85.4 |
| Comparative Example 2 | Rh(AcAc)(CO)$_2$ | TPP | 100 | 70 | 3.6 | 26.4 |
| Comparative Example 3 | Rh(AcAc)(CO)$_2$ | TPP | 100 | 100 | 8.0 | 177.2 |
| Comparative Example 4 | Rh(AcAc)(CO)$_2$ | ISO-44 | 3 | 85 | 9.5 | 219.3 |
| Comparative Example 5 | Rh(AcAc)(CO)$_2$ | BISBI | 3 | 85 | 20.7 | 88.8 |
| Comparative Example 6 | Rh(AcAc)(CO)$_2$ | BISBI | 10 | 85 | 21.0 | 79.9 |
| Comparative Example 7 | Rh(AcAc)(CO)$_2$ | BPNP-0 | 1 | 85 | 1.1 | 21.9 |

As shown in Table 4, in Comparative Example 1, in which hydroformylation reaction of propene was performed using a monodentate phosphorous compound, TPP, catalytic activity was 85.4 mol$_{(BAL)}$/mol$_{(Rh)}$/h, and N/I selectivity was 3.9. In Comparative Examples 2-3, in which hydroformylation reaction of propene was performed using the same catalyst system as in Comparative Example 1 at a temperature of 70° C. and 100° C., respectively, the catalytic activity (177.2 mol$_{(BAL)}$/mol$_{(Rh)}$/h) of Comparative Example 3 was remarkably greater than that (26.4 mol$_{(BAL)}$/mol$_{(Rh)}$/h) of Comparative Example 2. N/I selectivity was also remarkably increased with increasing reaction temperature (3.6 and 8.0).

Among currently available ligands, ISO-44 is known to be the most excellent for catalytic activity and N/I selectivity. It is also known that ISO-44 has been still applied in some processes under the trade name MARK-IV. In Comparative Example 4, in which hydroformylation reaction of propene was performed using a catalyst modified with ISO-44, catalytic activity was 219.3 mol$_{(BAL)}$/mol$_{(Rh)}$/h, and N/I selectivity was 9.5.

In Comparative Examples 5-6, in which hydroformylation reaction of propene was performed using BISBI, a very high tions, the catalytic activity of Comparative Example 4 was about 30% higher than that of Example 3. However, the N/I selectivity of Comparative Example 4 was 9.5, whereas the N/I selectivity of Example 3 was 23.6 which was 2.5 times that of Comparative Example 4. That is, it can be seen that even though the catalytic activity of BPNP-1 is slightly lower than that of ISO-44, BPNP-1 exhibits very high selectivity to normal-aldehyde.

In Examples 5-9, in which hydroformylation reaction of propene was performed at a 3:1 molar ratio of BPNP-1 to rhodium and at different temperatures from 70 to 110° C., as the reaction temperature increased, catalytic activity almost linearly increased and N/I selectivity also slightly increased, i.e., from 23 to 31. Such an increase in catalytic activity with increasing reaction temperature was also observed in Comparative Examples 2-3. However, Rh/PBNP-1 exhibited better catalytic activity than Rh/TPP at the same temperature condition. In addition, no change in color of the reactant solution was observed at low reaction temperatures and high reaction temperatures in Examples 5-9. This shows that a BPNP-1-modified catalyst is very stable under the above conditions.

Table 3 shows the catalytic activity and N/I selectivity of Examples 10-13 using as a ligand 2,2'-bis[N-(dipyrrolylphosphino)methylamino]-1,1'-biphenyl (BPNP-2) in which phenyl groups of $R_1$ and $R_2$ of BPNP-1 were substituted by pyrroles. In Examples 10-11, in which a molar ratio of BPNP-2 to rhodium was relatively low, catalytic activity was higher than Examples 1-7 in which BPNP-1 was used. However, in Examples 12-13, as the molar ratio of BPNP-2 to rhodium increased, catalytic activity gradually reduced. This phenomenon was also observed in Comparative Examples 5-6 using BISBI. However, when BPNP-1 was used, the N/I selectivity value was about 23 due to very high selectivity to normal-aldehyde. When BPNP-2 was used, the N/I selectivity value was 3.6 or less due to high selectivity to iso-aldehyde.

From the above results, it can be seen that an acetylacetonatodicarbonylrhodium (Rh(AcAc)(CO)$_2$) catalyst modified with a bidentate ligand, 2,2'-bis[N-(diphenylphosphino)methylamino]-1,1'-bipehnyl (BPNP-1), exhibits high catalytic activity of 65% or more and high selectivity to normal-aldehyde compared to commercially widely available Rh/TPP. Furthermore, catalytic activity and N/I selectivity are stably retained even at a high reaction temperature. In addition, a catalyst modified with 2,2'-bis[N-(dipyrrolylphosphino)methylamino]-1,1'-biphenyl (BPNP-2) in which phenyl groups of $R_1$ and $R_2$ of BPNP-1 are substituted by pyrrole groups exhibits very high catalytic activity and high selectivity to iso-aldehyde.

What is claimed is:

1. A catalyst composition comprising:
   (a) a bidentate ligand represented by formula 1 below; and
   (b) a transition metal catalyst represented by formula 2 below:

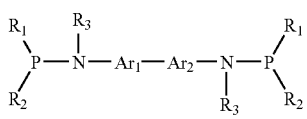

(1)

wherein, $R_1$ and $R_2$ are each a substituted or unsubstituted alkyl group of 1-20 carbon atoms, a substituted or unsubstituted alkoxy group of 1-20 carbon atoms, a substituted or unsubstituted cycloalkane or cycloalkene of 5-20 carbon atoms, a substituted or unsubstituted aryl group of 6-36 carbon atoms, a substituted or unsubstituted heteroalkyl group of 1-20 carbon atoms, a substituted or unsubstituted heteroaryl group of 4-36 carbon atoms, or a substituted or unsubstituted hetero ring group of 4-36 carbon atoms;

$Ar_1$—$Ar_2$ is a bisaryl compound, wherein the bisaryl compound of the bidentate ligand represented by formula 1 is a compound represented by formula 5 below:

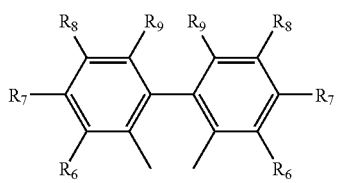

(5)

wherein, $R_6$, $R_7$, $R_8$, and $R_9$ are each hydrogen, an alkyl group of 1-20 carbon atoms, an aryl group of 6-20 carbon atoms, a triarylsilyl group, trialkylsilyl group, a carboalkoxy group represented by —CO$_2$R where R is an alkyl group of 1-20 carbon atoms or an aryl group of 6-20 carbon atoms, a carboaryloxy group, an aryloxy group, an alkoxy group, an alkylcarbonyl group, an arylcarbonyl group, an amide, a halogen, or a nitrile group; and $R_3$ is an alkyl group of 1-20 carbon atoms, an aryl group of 6-20 carbon atoms, a triarylsilyl group, a trialkylsilyl group, a carboalkoxy group represented by —CO$_2$R where R is an alkyl group of 1-20 carbon atoms or an aryl group of 6-20 carbon atoms, a carboaryloxy group, an aryloxy group, an alkoxy group, an alkylcarbonyl group, an arylcarbonyl group, an amide, a halogen, or a nitrile group, and $$M(L_1)_l(L_2)_m(L_3)_n \qquad (2)$$

wherein,

M is a transition metal;

$L_1$, $L_2$ and $L_3$ are each hydrogen, CO, acetylacetonato, cyclooctadiene, norbornene, chlorine, or triphenylphosphine; and l, m, and n are each an integer of 0 to 5, and the sum of l, m and n is not zero.

2. The catalyst composition of claim 1, wherein $R_1$ and $R_2$ of the bidentate ligand represented by formula 1 are each a phenyl group, a phenyloxy group, an alkyl group, an alkyloxy group, or a pyrrole group.

3. The catalyst composition of claim 1, wherein $R_3$ of the bidentate ligand represented by formula 1 is a methyl group, an ethyl group, a phenyl group, or an acetyl group (CH$_3$C(O)—).

4. The catalyst composition of claim 1, wherein in the compound represented by formula 5, $R_6$ is a methyl group, a methoxy group, or a tert-butyl group, $R_7$ is hydrogen, $R_8$ is a methyl group, a methoxy group, or a tert-butyl group, and $R_9$ is hydrogen or a methyl group.

5. The catalyst composition of claim 1, wherein the transition metal of the transition metal catalyst represented by formula 2 is cobalt (Co), rhodium (Rh), or iridium (Ir).

6. The catalyst composition of claim 1, wherein the transition metal catalyst is acetylacetonatodicarbonylrhodium (Rh(AcAc)(CO)$_2$), acetylacetonatocarbonyltriphenylphosphinerhodium (Rh(AcAc)(CO)(TPP)), hydridocarbonyltri(triphenylphosphine)rhodium (HRh(CO)(TPP)$_3$), acetylacetonatodicarbonyliridium (Ir(AcAc)(CO)$_2$), or hydridocarbonyltri(triphenylphosphine)iridium(HIr(CO)(TPP)$_3$).

7. The catalyst composition a of claim 1, wherein the content of the transition metal is in the range from 50 to 500 ppm based on the total concentration of a catalytic reaction solution, and the content of the bidentate ligand is in the range from 0.5 to 100 moles based on 1 mole of the transition metal.

8. The catalyst composition of claim 1, wherein the transition metal catalyst is acetylacetonatodicarbonylrhodium (Rh(AcAc)(CO)$_2$), and the bidentate ligand is 2,2'-bis[N-(diphenylphosphino)methylamino]1,1'-biphenyl (BPNP-1) or 2,2'-bis[N-(dipyrrolylphosphino)methylamino]-1,1'-biphenyl (BPNP-2).

9. A process for hydroformylation reaction of an olefin compound to prepare an aldehyde which comprising stirring the catalyst composition of claim 1, the olefin compound, and a gas mixture of carbon monoxide and hydrogen, under high temperature and pressure condition.

10. The process of claim 9, wherein the olefin compound is a compound represented by formula 3 below:

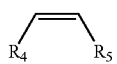
(3)

wherein, $R_4$ and $R_5$ are each hydrogen, an alkyl group of 1-20 carbon atoms, fluorine (—F), chlorine (—Cl), bromine (—Br), trifluoromethyl (—CF$_3$), or a phenyl group of 6-20 carbon atoms that may be unsubstituted or substituted by one to five substituents selected from the group consisting of a nitro group (—NO$_2$), fluorine (—F), chlorine (—Cl), bromine (—Br), a methyl group, an ethyl group, a propyl group, and a butyl group.

11. The process of claim 9, wherein the olefin compound is selected from the group consisting of ethene, propene, 1-butene, 1-pentene, 1-hexene, 1-octene, and styrene.

* * * * *